United States Patent [19]

Comiotto et al.

[11] Patent Number: 4,718,986
[45] Date of Patent: Jan. 12, 1988

[54] PROCESS FOR PRODUCTING HIGH PURITY BUTENE-1 WITH A LOW ENERGY CONSUMPTION

[75] Inventors: Renzo Comiotto; Bruno De Maglie, both of Milan, Italy

[73] Assignee: Snamprogetti, S.p.A., Milan, Italy

[21] Appl. No.: 904,046

[22] Filed: Sep. 4, 1986

Related U.S. Application Data

[63] Continuation-in-part of Ser. No. 633,879, Jul. 24, 1984, abandoned.

[30] Foreign Application Priority Data

Jul. 28, 1983 [IT] Italy ........................ 22293 A/83

[51] Int. Cl.$^4$ .............................................. B01D 1/28
[52] U.S. Cl. .......................................... 203/26; 203/32; 203/38; 203/80; 203/DIG. 8; 585/809
[58] Field of Search ............... 203/32, 21, 26, DIG. 6, 203/DIG. 8, 71, 73, 80, DIG. 9, 38; 585/809, 800, 699

[56] References Cited

U.S. PATENT DOCUMENTS

| | | | |
|---|---|---|---|
| 2,509,136 | 5/1950 | Cornell | 203/21 |
| 2,619,814 | 12/1952 | Kniel | 203/26 |
| 4,018,843 | 4/1977 | Michaux et al. | 585/854 |
| 4,137,129 | 1/1979 | Bjorklund | 203/26 |
| 4,162,198 | 7/1979 | Stocburger et al. | 585/865 |
| 4,230,535 | 10/1980 | Howard | 203/26 |
| 4,277,268 | 7/1981 | Spangler, Jr. | 62/30 |
| 4,336,407 | 6/1982 | Smith, Jr. | 203/DIG. 6 |
| 4,360,405 | 11/1982 | Tsao | 203/26 |
| 4,391,677 | 7/1983 | Harris et al. | 203/32 |
| 4,395,310 | 7/1983 | Idenden | 203/DIG. 4 |
| 4,555,312 | 11/1985 | Ogura | 203/29 |
| 4,569,725 | 2/1986 | Lindner et al. | 203/29 |

FOREIGN PATENT DOCUMENTS

| | | | |
|---|---|---|---|
| 2823570 | 12/1978 | Fed. Rep. of Germany | 203/DIG. 4 |
| 3011881 | 2/1978 | Japan | 203/DIG. 4 |
| 2035813 | 6/1980 | United Kingdom | 203/DIG. 4 |

Primary Examiner—S. Leon Bashore
Assistant Examiner—V. Manoharan
Attorney, Agent, or Firm—Morgan & Finnegan

[57] ABSTRACT

High purity butene-1, in particular polymerization grade butene-1, is obtained by means of a two-stage fractionation of a C$_4$ hydrocarbon stream comprising butene-1 which is substantially free from butadiene.

The first stage of the fractionation process allows practically all the isobutane contained in the C$_4$ batch to be separated as the top stream.

The bottom phase of the first stage of fractionation is supplied to the second stage of fractionation thus obtaining high purity butene-1 as the top fraction, and the remaining components as the bottom phase According to the process of the invention, vapors of butene-1 obtained as the top stream from the second stage of fractionation are compressed and the resultant heat of condensation is used for operating the reboilers of the two fractionation stages.

15 Claims, 1 Drawing Figure

U.S. Patent
Jan. 12, 1988
4,718,986
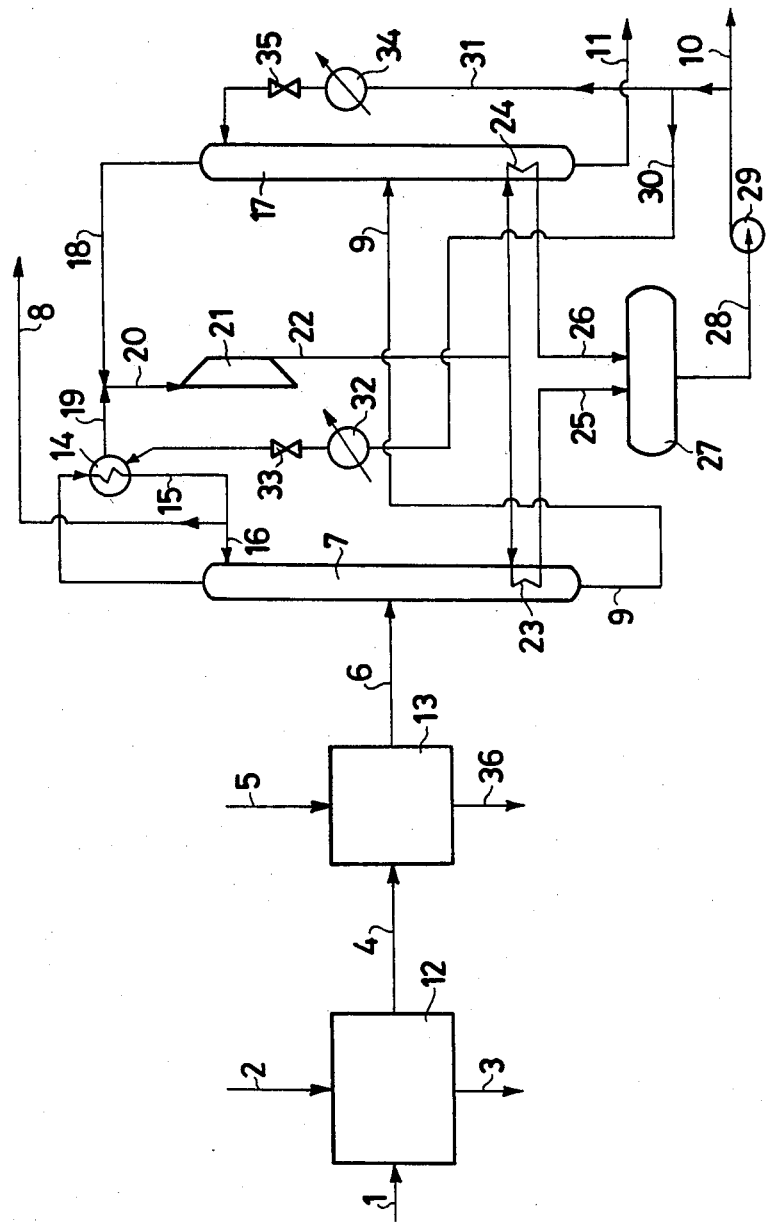

PROCESS FOR PRODUCING HIGH PURITY BUTENE-1 WITH A LOW ENERGY CONSUMPTION

This application is a continuation-in-part of Ser. No. 633,879, filed July 24, 1984 now abandoned.

The present invention relates to a process for the production of high purity butene-1 with low consumption of energy.

More particularly, the present invention relates to a process for the production of polymerization grade butene-1 with a low energy consumption.

Consumption of butene-1 has recently increased, in particular, in its use as a co-monomer in the production of low density linear polyethylene (LLDPE).

Other uses of butene-1 are in the production of polybutene-1, which has good stability at high temperature, and is a co-monomer in the production of high density polyethylene.

Butene-1 is normally contained in $C_4$ streams from refinery or steam cracking processes. Such streams, which are of interest herein, contain variable amounts, according to their origin, of isobutane, n-butane, isobutene, 1-butene, trans- and cis- 2-butene, reduced amounts of $C_3$ and $C_5$ hydrocarbons and possibly butadiene and acetylenic hydrocarbons (methyl-acetylene, propadiene, ethyl-acetylene, and vinyl-acetylene).

If butadine is contained in appreciable amounts, e.g., in $C_4$ streams originating from stream cracking processes, the butadiene must be extracted from the stream in a suitable extraction unit.

$C_4$ fractions which originate from streams from stream cracking or from fluid catalytic cracking processes, after the separation of butadiene, generally comprise compositions within the following ranges:

| | |
|---|---|
| $C_3$ components | 0.2–1.5% by weight |
| Isobutane | 1–30% by weight |
| Isobutene | 1–60% by weight |
| n-Butane | 3–20% by weight |
| Butene-1 | 10–40% by weight |
| cis- and trans- Butene-2 | 8–30% by weight |
| $C_5$ components | 0.1–1% by weight |
| Butadiene + Acetylenic derivatives | 0.1–6% by weight |

It has surprisingly been found that butene-1 can be obtained with high purity characteristics and at a low consumption of energy, from a stream having a composition as shown above, after that stream has been deprived of butadiene and acetylenic derivatives as thoroughly as possible (i.e., to an end concentration of from 30 to 200 ppm) by means of known processes.

The process according to the present invention comprises the following stages: (1) a substantially free from butadiene stream is fed to an etherifying unit wherein isobutene reacts with a saturated aliphatic alcohol, particularly chosen between methanol and/or ethanol, in the presence of a heterogeneous catalyst with functional sulphonic groups on a styrene-divinylbenzene matrix, in particular of the Amberlyst type, obtaining the corresponding tertiary butyl ether or ethers;

(2) the tertiary butyl ether or ethers thus obtained is/are separated by distillation from the remaining unreacted part of the stream in the same reaction vessel or in a distillation zone separated from the reaction zone; the ether-free product will be indicated hereinafter as "refined stream";

(3) the refined stream is submitted to a hydrogenating stage to selectively hydrogenate the butadiene and the acetylenic derivatives thus reducing their contents to a total value within the range of from 30 to 200 ppm, the selective hydrogenation is effected in the presence of a suitable and known catalyst at a temperature within the range of from 35° C. to 50° C. and at a pressure within the range of from 40 to 20 abs. atm., thus, minimizing the isomerization of butene-1 to butene-2;

(4) the refined stream, after having been selectively hydrogenated, is fed to a first stage of fractionation operated at a pressure within a range of from 4 abs. atm. to 20 abs. atm., and preferably from 8 to 12 abs. atm., obtaining as the top stream isobutane and a reduced amount of butene-1 and a bottom stream containing the remaining components of the batch;

(5) the bottom stream from the first fractionation stage is fed to a second fractionation stage operated at a pressure within the range of from 4 abs. atm. to 12 abs. atm. and preferably at a pressure in the range of from 6 to 10 abs. atm., thus, obtaining a top stream consisting of high purity butene-1, particularly, polymerization grade butene-1 and a bottom stream containing n-butane, cis- and trans- butene-2 and a reduced amount of butene-1;

the process is characterized in that the top stream products originating from the second fractionation stage are compressed by means of a compressor and are then fed partly to the reboiler of the first fractionation stage, and the balance to the reboiler of the second fractionation stage to evaporate the bottom product of the two fractionation stages, the condensed butene-1 in the two reboilers being partly discharged as the end product and partly used in other stages of the process.

According to a preferred embodiment of the process according to the present invention the butene-1 which is not discharged as end product is partly fed to the top stream of the second fractionating stage, where it is used as reflux, and partly to the top condenser of the first fractionation stage where it is used, by means of its complete vaporing, as refrigerating fluid for condensing the top stream from the first fractionation stage which is partly reflowed and party discharged.

According to a particular embodiment of the process of the present invention, the butene-1 which is fed to the top stream of the second fractionation stage is used as reflux and/or the butene-1 which is fed to the condenser of the first fractionation stage is caused to expand before entering the second stage as reflux and the condenser of the first stage. During this expansion of butene-1 a volume of vapors of butene-1 is generated which, together with the vapors of butene-1 originating from the condenser of the first stage and those from the top stream of the second stage are fed, after a preliminary compression, to one or both of the reboilers of the two fractionation stages. The reboilers of the two fractionation stages can also be fed with a stream from the outside should the butene-1 not be enough, but this generally happens only when the butene-1 originating from the top stream of the second fractionation stage is fed to the reboilers.

It is interesting to note that by operating the process according to the present invention, in particular its preferred and particular embodiment, the exclusively used energy is that which is necessary for the compression stage and in addition, the use of only one compression stage and in addition, the use of only one compressing means for the mixture of the streams of butene-1 further reduces the operating costs of the process.

The process according to the present invention will now be illustrated with the aid of the attached drawing, which is not intended to limit the invention.

The hydrocarbon stream (1) containing isobutene, n-butane, isobutane, butene-1, cis- and trans- butene-2 and reduced percentages of $C_5$, $C_3$, butadiene and acetylenic hydrocarbons is fed to the etherifying unit (12), where it reacts with the methanol (2) producing methyl-tert-butyl ether (3) which is separated by known means from the remaining products in the stream. The stream (4) which is free from isobutene (refined stream) is fed to the selective hydrogenation unit (13) of the butadiene and of the acetylenic derivatives in which the butadiene and the acetylenic derivatives react with hydrogen (5).

The stream (36) represents nearly all the non-reacted hydrogen and a certain amount of $C_4$ fraction.

The hydrogenated refined stream (6) is fed to the distillation column (7) at a pressure within the range from 8 to 12 abs. atm., from the top of said column isobutane and a small amount of butene-1 being separated; the top stream from column (7) is condensed in the condenser unit (14) thus originating a liquid stream (15), essentially consisting of isobutane, which is partly used as reflux (16) and partly (8) discharged from the plant.

The bottom stream product (9) is fed to the distillation column (17) where from the top, high purity butene-1 (18) is separated, and from the bottom the remaining products of the refined stream (11) are separated.

Stream (18) is mixed with stream (19), originating from the condenser (14), thus forming the stream (20).

This last stream (20) is compressed by the compressor (21) from the pressure of 3 abs. atm. to an end pressure of from 10 to 20 abs. atm.

The compressed stream (22) is fed to the reboilers (23) and (24) of the two columns (7) and (17) respectively and the condensates (25) and (26) are introduced in the vessel (27).

The liquid butene-1 (28) from the vessel (27) passes through the pump (29) and is partly discharged (10) and partly divided into two streams (30) and (31).

The second butene-1 stream (30) is cooled at (32), expanded in the expansion valve (33) to a pressure of about 3 abs. atm. and then fed as the refrigerating fluid to the condenser (14).

The first butene-1 in the stream (31) is cooled at (34), expanded in (35) to the pressure existing in the column (17) and finally introduced as reflux to column (17).

The process will now be described with reference to the attached drawing and the following tables for a batch comprising the compositions indicated. The extreme purity of the butene-1 product obtained by the process of the invention is evident from the tables.

| | Position | | | | | | | | | | | |
|---|---|---|---|---|---|---|---|---|---|---|---|---|
| | 1 | | 4 | | 5 | | 6 | | 36 | | 8 | |
| | Kg/hr | % wt | Kg/hr | % wt | Kg/hr | % wt | Kg/hr | % wt | Kg/hr | % wt | kg/hr | % wt |
| $H_2$ | — | — | — | — | 6 | 100.0 | 1 | | 2 | 1.5 | 1 | |
| $C_3$ Hdrocarbons | 90 | 0.9 | 90 | 0.9 | — | — | 90 | 0.9 | 6 | 4.5 | 90 | 3.3 |
| Isobutane | 2360 | 23.6 | 2360 | 24.5 | — | — | 2360 | 24.8 | 39 | 29.6 | 2359 | 86.7 |
| Isobutene | 220 | 2.2 | 10 | 0.1 | — | — | 10 | 0.1 | — | — | 2 | 0.1 |
| Butene-1 | 3090 | 30.9 | 3075 | 31.9 | — | — | 2831 | 29.7 | 41 | 31.1 | 259 | 9.5 |
| 1,3-Butadiene | 70 | 0.7 | 70 | 0.7 | — | — | — | — | — | — | —. | — |
| n-Butane | 1730 | 17.3 | 1730 | 17.9 | — | — | 1814 | 19.1 | 18 | 13.6 | 5 | 0.2 |
| trans-Butene-2 | 1430 | 14.3 | 1440 | 14.9 | — | — | 1511 | 15.9 | 17 | 12.9 | 4 | 0.2 |
| cis-Butene-2 | 870 | 8.7 | 875 | 9.1 | — | — | 907 | 9.5 | 9 | 6.8 | 1 | |
| $C_5$ Hydrocarbons | 140 | 1.4 | — | — | — | — | — | — | — | — | — | — |
| TOTAL | 10000 | 100.0 | 9650 | 100.0 | 6 | 100.0 | 9524 | 100.0 | 132 | 100.0 | 2721 | 100.0 |
| Physical state | LIQUID | | LIQUID | | GAS | | LIQUID | | GAS | | LIQUID | |
| Temperature °C. | 40 | | 40 | | 35 | | 50 | | 35 | | 40 | |
| Pressure (abs. atm.) | 5 | | 8 | | 9 | | 11 | | 7 | | 9 | |

| | Position | | | | | | | | | | | |
|---|---|---|---|---|---|---|---|---|---|---|---|---|
| | 9 | | 10 | | 11 | | 18 | | 19 | | 25 | |
| | Kg/hr | % wt | Kg/hr | % wt | Kg/hr | % wt | Kg/hr | % wt | Kg/hr | % wt | Kg/hr | % wt |
| $H_2$ | — | — | — | — | — | — | — | — | | | — | — |
| $C_3$ Hdrocarbons | — | — | — | — | — | — | — | — | | | — | — |
| Isobutane | 1 | | 1 | 0.1 | — | — | 42 | 0.1 | | | 43 | 0.1 |
| Isobutene | 8 | 0.1 | 8 | 0.3 | — | — | 333 | 0.3 | | | 347 | 0.3 |
| Butene-1 | 2572 | 37.8 | 2557 | 99.0 | 15 | 0.4 | 106474 | 99.0 | | | 110769 | 99.9 |
| 1,3-Butadiene | — | — | — | 50 PPM | — | — | — | — | | | — | — |
| n-Butane | 1809 | 26.6 | 14 | 0.5 | 1795 | 42.5 | 583 | 0.5 | | | 606 | 0.5 |
| trans-Butene-2 | 1507 | 22.2 | 2 | 0.1 | 1505 | 35.7 | 83 | 0.1 | | | 87 | 0.1 |
| cis-Butene-2 | 906 | 13.3 | — | — | 906 | 21.4 | — | — | | | — | — |
| $C_5$ Hydrocarbons | — | — | — | — | — | — | — | — | | | — | — |
| TOTAL | 6803 | 100.0 | 2582 | 100.0 | 4221 | 100.0 | 107515 | 100.00 | same as 30 | | 111852 | 100.00 |
| Physical state | LIQUID | | LIQUID | | LIQUID | | VAPOR | | VAPOR | | LIQUID | |
| Temperature °C. | 80 | | 40 | | 40 | | 45 | | 28 | | 90 | |
| Pressure (abs. atm.) | 11 | | 8 | | 8 | | 5 | | 3 | | 15.3 | |

-continued

| | | Position | | | | | | | |
|---|---|---|---|---|---|---|---|---|---|
| | | 22 | | 30 | | 31 | | 26 | |
| | | Kg/hr | % wt | Kg/hr | % wt | kg/hr | % wt | Kg/hr | % wt |
| | $H_2$ | — | — | — | — | — | — | — | — |
| | $C_3$ Hdrocarbons | — | — | — | — | — | — | — | — |
| | Isobutane | 84 | 0.1 | 42 | 0.1 | 41 | 0.1 | 40 | 0.1 |
| | Isobutene | 672 | 0.3 | 339 | 0.3 | 325 | 0.3 | 325 | 0.3 |
| | Butene-1 | 214676 | 99.9 | 108202 | 99.0 | 103917 | 99.0 | 103908 | 99.0 |
| | 1,3-Butadiene | — | — | — | — | — | — | — | — |
| | n-Butane | 1175 | 0.5 | 592 | 0.5 | 569 | 0.5 | 569 | 0.5 |
| | trans-Butene-2 | 168 | 0.1 | 85 | 0.1 | 81 | 0.1 | 81 | 0.1 |
| | cis-Butene-2 | — | — | — | — | — | — | — | — |
| | $C_5$ Hydrocarbons | — | — | — | — | — | — | — | — |
| | TOTAL | 216775 | 100.0 | 109260 | 100.0 | 104933 | 100.0 | 104923 | 100.0 |
| | Physical state | VAPOR | | LIQUID | | LIQUID | | LIQUID | |
| | Temperature °C. | 100 | | 90 | | 90 | | 90 | |
| | Pressure (abs. atm.) | 15.7 | | 15 | | 15 | | 15.3 | |

What is claimed is:

1. A process for the production of high purity butene-1 at low energy consumption comprising the steps of:
    etherifying an isobutene component of a raw material $C_4$ stream with a saturated aliphatic alcohol to substantially eliminate the etherified isobutene from said $C_4$ stream;
    submitting the $C_4$ stream to a selective hydrogenation to reduce the content of butadiene and acetylenic derivatives to a total of from 30 to 200 ppm of the $C_4$ stream;
    feeding the selectively hydrogenated $C_4$ stream to a first stage of fractionation at a pressure in the range of from 4 to 20 abs. atm. from which a top stream product consisting of isobutane and a portion of butene-1 and a bottom stream of residual components from the $C_4$ stream are obtained from the first fractionation stage;
    feeding the bottom stream from the first stage of fractionation of residual components to a second stage of fractionation at a pressure in the range of from 4 to 12 abs. atm. from which a top stream comprising high purity butene-1 and a bottom stream comprising n-butane, trans- and cis- butene-2 and a remaining portion of butene-1 are obtained;
    compressing the top butene-1 stream from the second stage of fractionation;
    feeding a portion of the compressed butene-1 stream to a reboiler of the first fractionation stage and the other portion of the compressed butene-1 stream to a reboiler of the second fractionation stage, whereby the butene-1 stream portions are condensed; and
    discharging the condensed butene-1 streams as an end product.

2. A process according to claim 1, wherein subjecting at least a portion of the condensed butene-1 stream, prior to discharging the condensed butene-1 as an end product, to the additional step of:
    utilizing at least a portion of the condensed butene-1 stream in operations of the process including use as a reflux for the second fractionation stage and a coolant for condensing isobutane obtained in the top stream of the first fractionation stage.

3. A process according to claim 1, wherein a portion of the condensed butene-1 stream is subjected, prior to discharging as an end product, to an additional step of:
    feeding a portion of the condensed butene-1 to a top section of the second fractionation stage, wherein, the condensed butene-1 is utilized as a reflux for said second fractionation stage.

4. A process according to claim 1, wherein, a portion of the condensed butene-1 stream is subjected, prior to discharging as an end product, to an additional step of:
    feeding a portion of the condensed butene-1 to a top section of the first fractionation stage, wherein, a butene-1 vapor is utilized as a coolant for condensing the top stream product of the first fractionation stage.

5. A process according to claim 4, wherein, the condensed isobutane obtained as a top stream of the first fractionation stage is utilized as a reflux in the first fractionation stage.

6. A process according to claim 2 wherein a first and second portion of the condensed butene-1 stream, prior to being discharged as an end product and utilized in operations of the process as a reflux and a coolant, respectively, is subjected to the additional step of:
    expanding said first and second portions of the condensed butene-1 to generate a reflux and cooling vapor, respectively.

7. A process according to claim 3, wherein, the portion of the condensed butene-1 stream prior to being discharged as an end product and utilized in operations of the process as a reflux is subjected to the additional step of:
    expanding a portion of the condensed butene-1 to generate a vapor.

8. A process according to claim 4, wherein, the portion of the condensed butene-1 stream prior to being discharged as an end product and utilized in operations of the process as a coolant is subjected to the additional step of:
    expanding a portion of the condensed butene-1 to generate the cooling vapor.

9. A process according to claim 5, wherein, the portion of condensed butene-1 stream prior to being utilized in operations of the process as a coolant is subjected to the additional step of:
    expanding a portion of the condensed butene-1 to generate a cooling vapor.

10. A process according to claim 4 wherein the butene-1 utilized as a coolant for condensing the top stream products of the first fractionation stage is subjected to the subsequent and additional steps of:
    compressing the coolant butene-1; and
    feeding the compressed butene-1 to supply heat to at least one reboiler of the first and second fractionation stages.

11. A process according to claim 6 wherein the butene-1 utilized as a coolant for condensing the top stream products of the first fractionation stage is subjected to the subsequent and additional steps of:
compressing the coolant butene-1; and
feeding the compressed butene-1 to supply heat to at least one reboiler of the first and second fractionation stages.

12. A process according to claim 8 wherein the butene-1 utilized as a coolant for condensing the top stream products of the first fractionation stage is subjected to the subsequent and additional steps of:
compressing the coolant butene-1; and
feeding the compressed butene-1 to supply heat to at least one reboiler of the first and second fractionation stages.

13. A process according to claim 9 wherein the butene-1 utilized as a coolant for condensing the top stream products of the first fractionation stage is subjected to the subsequent and additional steps of:
compressing the coolant butene-1; and
feeding the compressed butene-1 to supply heat to at least one reboiler of the first and second fractionation stages.

14. A process for the production of high purity butene-1 at low energy consumption comprising the steps of:
etherifying an isobutene component of a raw material $C_4$ stream with a saturated aliphatic alcohol to substantially eliminate the etherified isobutene from said $C_4$ stream;
submitting the $C_4$ stream to a selective hydrogenation to reduce the content of butadiene and acetylenic derivatives to a total of from 30 to 200 ppm of $C_4$ stream;
feeding the selectively hydrogenated $C_4$ stream to a first stage of fractionation at a pressure in the range of from 4 to 20 abs. atm. from which a top stream product consisting of isobutane and a portion of butene-1 and a bottom stream of residual components from the $C_4$ stream are obtained from the first fractionation stage;
feeding the bottom stream from the first stage of fractionation of residual components to a second stage of fractionation at a pressure in the range of from 4 to 12 abs. atm. from which a top stream comprising high purity butene-1 and a bottom stream comprising n-butane, trans- and cis- butene-2 and a remaining portion of butene-1 are obtained;
compressing the top butene-1 stream from the second stage of fractionation;
feeding a portion of the compressed butene-1 stream to a reboiler of the first fractionation stage and the other portion of the compressed butene-1 stream to a reboiler of the second fractionation stage, whereby the butene-1 stream portions are condensed;
utilizing at least a portion of the condensed butene-1 stream in operations of the process including use as a reflux for the second fractionation stage and a coolant for condensing isobutane obtained in the top stream of the first fractionation stage, wherein a first portion of the condensed butene-1 is fed to a top section of the second fractionation stage and utilized as a reflux for said second fractionation stage and a second portion of the condensed butene-1 is fed to a top section of the first fractionation stage, wherein, the butene-1 vapor is utilized as a coolant for condensing the top stream product of the first fractionation stage; and
discharging a remaining portion of the condensed butene-1 stream as an end product.

15. A process for the production of high purity butene-1 at low energy consumption comprising the steps of:
etherifying an isobutene component of a raw material $C_4$ stream with a saturated aliphatic alcohol to substantially eliminate the etherified isobutene from said stream;
submitting the $C_4$ stream to a selective hydrogenation to reduce the content of butadiene and acetylenic derivatives to a total of from 30 to 200 ppm of the $C_4$ stream;
feeding the selectively hydrogenated $C_4$ stream to a first stage of fractionation at a pressure in the range of from 4 to 20 abs. atm. from which a top stream product consisting of isobutane and a portion of butene-1 and a bottom stream of residual components from the $C_4$ stream are obtained from the first fractionation stage;
feeding the bottom stream from the first stage of fractionation of residual components to a second stage of fractionation at a pressure in the range of from 4 to 12 abs. atm. from which a top stream comprising high purity butene-1 and a bottom stream comprising n-butane, trans-, and cis-butene-2 and a remaining portion of butene-1 are obtained;
compressing the top butene-1 stream from the second stage of fractionation;
feeding a portion of the compressed butene-1 stream to a reboiler of the first fractionation stage and the other portion of the compressed butene-1 stream to a reboiler of the second fractionation stage, whereby the butene-1 stream portions are condensed;
utilizing at least a portion of the condensed butene-1 stream in operations of the process including use as a reflux for the second fractionation stage and a coolant for condensing isobutane obtained in the top stream of the first fractionation stage, wherein a portion of the condensed butene-1 is expanded to create a vapor and is fed to a top section of the second fractionation stage and utilized as a reflux for said second fractionation stage and a second portion of the condensed butene-1 is fed to a top section of the first fractionation stage, wherein, the butene-1 is subjected to expansion and utilized as a coolant vapor for condensing the top stream product of the first fractionation stage;
compressing the coolant vapor butene-1 and feeding the compressed butene-1 to supply heat to at least one reboiler of the first and second fractionation stages; and
discharging the condensed butene-1 streams as end product.

* * * * *